US006797290B2

(12) United States Patent
Dartey et al.

(10) Patent No.: US 6,797,290 B2
(45) Date of Patent: Sep. 28, 2004

(54) COMPOSITIONS FOR APPETITE CONTROL AND RELATED METHODS

(75) Inventors: Clemence Dartey, Ambler, PA (US); Gilbert Leveille, Denville, NJ (US); Thomas E. Sox, Ambler, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 350 days.

(21) Appl. No.: 09/953,784

(22) Filed: Sep. 17, 2001

(65) Prior Publication Data

US 2003/0059495 A1 Mar. 27, 2003

(51) Int. Cl.[7] .......................... A01N 37/18; A23L 1/308
(52) U.S. Cl. .......................... 426/2; 426/648; 426/590; 426/656; 426/658; 426/661; 514/2; 514/773; 514/775; 514/783; 514/55
(58) Field of Search .......................... 426/2, 648, 656, 426/658, 661, 590; 514/2, 775, 773, 55

(56) References Cited

U.S. PATENT DOCUMENTS

| | | | |
|---|---|---|---|
| 4,223,023 A | * | 9/1980 | Furda .......................... 514/55 |
| 4,427,658 A | | 1/1984 | Maubois et al. |
| 5,061,622 A | | 10/1991 | Dosako et al. |
| 5,075,424 A | | 12/1991 | Tanimoto et al. |
| 5,104,674 A | | 4/1992 | Chen et al. |
| 5,216,129 A | | 6/1993 | Berrocal et al. |
| 5,278,288 A | | 1/1994 | Kawasaki et al. |
| 5,280,107 A | | 1/1994 | Kawasaki et al. |
| 5,364,636 A | | 11/1994 | Ochi |
| 5,609,904 A | | 3/1997 | Koh et al. |
| 5,780,439 A | | 7/1998 | Mendy et al. |
| 5,932,561 A | | 8/1999 | Meyers et al. |
| 5,968,586 A | | 10/1999 | Etzel |
| 6,207,638 B1 | * | 3/2001 | Portman .......................... 514/2 |
| 6,323,189 B1 | * | 11/2001 | Hardinge-Lyme .......... 514/55 |
| 6,436,899 B2 | * | 8/2002 | Portman .......................... 514/2 |
| 6,468,962 B1 | * | 10/2002 | Portman .......................... 514/2 |

FOREIGN PATENT DOCUMENTS

| | | |
|---|---|---|
| EP | 0 841 011 * | 5/1998 |
| EP | 0876816 A1 | 11/1998 |
| GB | 2179043 A | 2/1987 |
| WO | WO 99/21566 A | 5/1999 |
| WO | WO 99/38393 A2 | 8/1999 |
| WO | WO 00/05974 A1 | 2/2000 |
| WO | WO 00/50090 A2 | 8/2000 |
| WO | WO 01/08507 A1 | 2/2001 |
| WO | WO 01/25414 A1 | 4/2001 |
| WO | WO 01/32038 A1 | 5/2001 |
| WO | WO 01/62086 A | 8/2001 |

OTHER PUBLICATIONS

PCT Search Report for PCT/US 02/29300 dated Jan. 17, 2003.

James W. Anderson et al.; Soluble Fiber Hypocholesterolemic Effects and Proposed Mechanisms; Dietary Fiber Chemistry, Physiology, and Health Effects; pp. 339–363.

T.Corring et al.; Release of Cholecystokinin in People After Ingestion of Glycomacropeptide (GMP); Abstracts of paper Presentations from the International Whey Conference 1997.

Gallaher et al.; Cholesterol Reduction by Glucomannan and Chitosan is Mediated by Changes in Cholesterol Absorption and Bile Acid and Fat Excretion in Rats [1,2,3] ; Nutrient Metabolism; 2000 American Society for Nutritional Sciences, pp. 2753–2759.

Kawasaki et al.; Inhibition by k–Casein Glycomacropeptide and Lactoferrin of Influenza Virus Hemagglutination; Bioscil. Biotech Biochem., 57(7), 1993; pp. 1214–1215.

Koop et al.; Physiological control of cholecystokinin release and pancreatic enzyme secretion by intraduodenal bile acids; Gut 1996; 39; pp. 661–667.

Muzzarelli; Chitosan–based dietary foods; Carbohydrate Polymers 29 (1996); pp. 309–316.

Muzzarelli; Human enzymatic activities related to the therapeutic administration of chitin derivatives; CMLS, Cell. mol. life sci. 53 (1997); pp. 131–140.

Tanimoto et al.; Large–scale Preparation of k–Casein Glycomacropeptide from Rennet Casein Whey; Biosci. Biotech. Biochem., 56(1), 1992; pp. 140–141.

Nakano et al.; Purification of Glycomacropeptide from Caseinate Hydrolysate by Gel Chromatography and Treatment with Acidic Solution; Journal of Food Science, vol. 65, No. 4, 2000; pp. 588–590.

Tanimoto et al.; Large–scale preparation of k–Casein Glycomacropeptide from Rennet Casein Whey; Biosci. Biotech. Biochem., 56(1), 1992; pp. 140–141.

Ormrod et al.; Dietary chitosan inhibits hypercholesterolaemia and atherogenesis in the apolipoprotein E–deficient mouse model of atherosclerosis; Atherosclerosis 138 (1998); pp. 329–334.

Yvon et al.; Effects of caseinomacropeptide (CMP) on digestoin regulation; Reprod Nutr Dev (1994) 34; pp. 527–537.

Beucher et al.: Effect of caseinomacropeptide (CMP) on cholecystokinin (CCK) release in rat; Reprod Nutr Dev 34 (1994); pp. 613–614.

* cited by examiner

Primary Examiner—N. Bhat
(74) Attorney, Agent, or Firm—Timothy E. Tracy

(57) ABSTRACT

The present invention is directed to a composition for oral administration that includes chitosan and GMP, wherein the chitosan and GMP are in other than a cationic gum or polysaccharide/protein complex. Also included herein are methods for controlling appetite in humans and animals by orally administering a composition that includes chitosan and GMP, wherein the chitosan and GMP are in other than a cationic gum or polysaccharide/protein complex.

37 Claims, No Drawings

COMPOSITIONS FOR APPETITE CONTROL AND RELATED METHODS

The present invention relates to the use of chitosan and glycomacropeptide for the preparation of food, beverage, and dietary supplement products intended for promoting weight loss through appetite control, e.g., inducing satiety and reducing appetite, as well as lowering of serum cholesterol and lipids.

BACKGROUND

Appetite control in animals is physiologically complex. Some important factors include emotional state, the physical state of the stomach and intestine, and the levels of multiple hormones. Cholecystokinin (CCK) is a hormone produced by cells of the intestinal epithelium in response to signals triggered by intake of nutrients. It is believed to be an important hormone for appetite regulation. CCK acts at multiple sites in the body, including the brain.

It is known that increased CCK levels decreases appetite and slows the rate of gastric emptying. Therefore, enhancing the onset of CCK production increases the total levels of CCK secreted, which results in a reduction of appetite, thereby decreasing the total amount of food consumed. Additionally, increased levels of CCK also result in inducing satiety, which is a state characterized by a reduced interest and perceived need for food. Long term increases in CCK result in a benefit of weight loss or reduced weight gain. Additionally, decreasing food consumption generally provides an improvement in the levels of serum cholesterol and total lipids.

CCK production is controlled by, among other things, a feedback control based upon the presence of bile acids, which are surfactant-like molecules and improve fat digestion by aiding in the dispersion and emulsification of fat or lipids.

After production in the liver, bile acids are stored in the gall bladder, which contracts and releases bile acids into the intestine in response to CCK. One group concluded that the presence of physiologic concentrations free of bile acids suppress CCK production. I. Koop et al., *Physiological Control of Cholecystokinin Release and Pancreatic Enzyme Secretion by Intraduodenal Bile Acids*, Gut 39:661–667 (1996).

Chitosan is an anionic polymer that is sometimes produced by the hydrolysis of crustacean shells. U.S. Pat. Nos. 4,223,023 and 5,932,561 disclose that chitosan binds to lipids. The resulting bound complex is resistant to digestion and absorption and is excreted in relatively unaltered form in the feces. As a result, the body is deprived of the large number of calories. Consequently, chitosan is widely used in food and dietary supplement products to promote weight loss.

U.S. Pat. No. 5,932,561 also discloses that chitosan reduces the amount of cholesterol available for absorption and assimilation by the body. Additionally, it has been found to reduce serum cholesterol levels. Cholesterol lowering by chitosan was extensively reviewed by J. W. Anderson et al. *Soluble Fiber*, pp. 339–363, in Dietary Fiber, Chemistry, Physiology, and Health Effects, eds. D. Kritchevsky, C. Bonfield, J. W. Anderson, Plenum Press, New York(1990). It was found that dietary chitosan, on a per gram basis, was more effective than pectin, guar gum, psyllium, or oat bran in lowering serum cholesterol in rats.

U.S. Pat. No. 5, 932,561 further discloses that chitosan also binds bile acids. Bile acids, such as deoxycholic acid, bear some structural similarities to cholesterol. One group found that when rats were fed a diet supplemented with chitosan, the level of fecal excretion of bile acids was greater than that observed in animals consuming a control diet, or in animals that had been fed a diet supplemented with similar levels of glucomannan. C. M. Gallaher, et al., *Cholesterol Reduction by Glucomannan and Chitosan Is Mediated by Changes in Cholesterol Absorption and Bile Acid and Fat Excretion in Rats*, J. Nutrition 130:2753–2759(2000). Thus, it was concluded that chitosan bound bile acids so avidly that the normal process of resorption of bile acids in the lower intestine was disrupted, and the bile acids were excreted in the feces.

Glycomacropeptide (GMP) is a glycopeptide that is produced from the proteolytic cleavage of κ-casein, a major dairy milk protein. GMP is present in the whey stream of cheese making, and commercial materials include whey isolates of varying purity. For example, Armor Proteines (Saint Brice en Cogles, France) supplies a material that is about 14% GMP. Glanbia Ingredients (Madison, Wis.) also supplies a whey protein isolate that contains about 16% GMP.

GMP has been found to increase CCK levels. The original research on GMP was performed in the early 1990's by M. Yvon, T. Corring, and colleagues at the Laboratoire de Recherches Laitieres, Rennes, France. Yvon et al., *Effects of Caseinmacropeptide (CMP) on Digestion Regulation*, Reprod. Nutr. Dev. 34:527–537 (1994). Yvon et al. described a material that they named casein macropeptide, or CMP, which was produced by the protease cleavage of κ-casein (κ-casein is one of four forms of casein found in diary milk, and represents 13% of casein). CMP was heterogeneous because of heterozygosity in the gene encoding the protein, as well as variation in the pattern of post-translational phosphorylation and glycosylation. Yvon et al. described four major fractions of CMP. *Effects of Gastric Digestive Products from Casein on CCK Release by Intestinal Cells in Rats*, J. Nutr. Biochem. 5:578–584(1994). The investigators infused each of four fractions into isolated rat ileal segments, and measured CCK release. Only one of the four fractions stimulated CCK production. A subsequent paper by these authors indicated that glycosylation of the peptide was necessary for increasing CCK levels, and CMP obtained from only one of the two genetic variants of bovine κ-casein (alpha variant) was effective. *Effect of Caseinmacropeptide (CMP) on Cholecystokinin (CCK) Release in Rat*, Reprod. Nutr. Dev. 34:613–614 (1994).

One study looked at the effects of ingested GMP on human CCK levels. Corring, T. et al., 1997 International Whey Conference, Abstracts of Paper Presentations, Chicago. This study involved six volunteers; two received 50 g of casein, two received 50 g of whey protein, and two received 25 mg of GMP (purified material that was a slightly glycosylated form of variant A). Serum CCK and gastrin levels were measured over four hours after ingestion of the test substances. All treatments increased CCK over baseline; casein produced a 350% increase, whey protein, a 415% increase, and GMP, a 268% increase. The results are especially surprising in light of the small amount of GMP consumed (casein and whey protein were consumed in levels 2000 times that of GMP). Interestingly, serum gastrin levels were increased by casein and whey protein, but not by GMP.

Numerous processes have been described for the enzymatic digestion of casein and the isolation of GMP. For example, see U.S. Pat. Nos. 4,427,658, 5,061,622, 5,075, 424, 5,216,129, 5,278,288, 5,280,107, 5,780,439, and 5,968, 586, which are incorporated herein by reference. Also, see T. Nakano and L. Ozimek, Purification of Glycomacropeptide from Caseinate Hydrolysate by Gel Chromatography and Treatment with Acidic Solution, J. of Food Science, 65:588–590 (2000), and M. Tanimoto, et al., Large Scale Preparation of κ-Casein Glycomacropeptide from Rennet Casein Whey, Biosci. Biotech. Biochem., 56:40–141 (1992), which are incorporated herein by reference.

From a pure lexicographical view, GMP and CMP are different terms. However, they have been used by those skilled in the art to describe essentially the same material. Therefore, these two terms are functionally equivalent. Additionally, this material has also been described in the literature as κ-casein glycomacropeptide. Y. Kawasaki et al., *Inhibition by κ-Casein Glycomacropeptide and Lactoferrin of Influenza Virus Hemagglutination*, Biosci. Biotech. Biochem. 57:1214–1215(1993).

U.S. Pat. No. 6,207,638 discloses a dry powder for enhancing satiety prior to a meal and extending satiety after a meal in a calorically efficient fashion. The dry powder was disclosed as containing 5.56–46.89% protein, 0.15–15.38% GMP, 5.56–46.8% oleic acid, 11.11–58.62% other long chain fatty acids, 5.56–46.89% soluble fiber and 2.70–37.36% insoluble fiber. The '638 patent discloses that by stimulating CCK release and blocking the negative feedback mechanism of CCK release, satiety is enhanced with the consumption of fewer calories and satiation effects can be extended for up to three hours following a meal.

Thus, increased CCK levels have been found by ingestion of chitosan, as a result of binding bile acids, thereby inhibiting bile acid feedback that controls CCK release, and GMP, as result of stimulating CCK release and blocking the negative feedback mechanism of CCK release. However, until the present invention, no single composition could increase CCK levels using both chitosan and GMP. Therefore, there is a need to provide a single composition containing both chitosan and GMP, as well as related methods for appetite control.

SUMMARY

The present invention is directed to a composition that satisfies the need for a single composition containing both chitosan and GMP, wherein the chitosan and GMP are in other than a cationic gum or polysaccharide/protein complex, as well as related methods for appetite control in a human and an animal.

DETAILED DESCRIPTION

As used herein, the term chitosan includes a biopolymer produced by the deacetylation of chitin, which is derived from exoskeletons of shellfish, such as crabs and shrimp, a compound that is a partially or completely deacetylated aminopolysaccharide derived from crustaceans or fungi, is obtained from fermentation processes, is obtained by de novo synthesis with isolated enzymes, or is obtained by synthesis using classic organic chemistry approaches.

As used in herein, the term "glycomacropeptide" or "GMP" refers to both substantially pure materials, e.g., CMP, GMP, and κ-casein glycomacropeptide, as well as the commercial materials containing a mixture of components.

As used herein, the term dietary supplement, refers to materials defined as dietary supplements in Section 3 of the Dietary Supplement Health and Education Act of 1994, Public Law 103-417, Oct. 25, 1994.

As used herein, the term appetite control refers to inducing satiety, reducing appetite, or both.

As used herein, all numerical ranges expressly include at least all numbers that fall between the endpoints of the ranges.

Excess weight and elevated blood cholesterol and lipids are endemic in modern society. Humans and other animals are known to have such afflictions. Thus, there is need for products that will reduce weight in human and other animals. One of the safest and most consumer acceptable ways of promoting weight loss is through decreasing appetite. This results in decreased food consumption. If the level of exercise is held constant, the individual loses weight or ceases to gain weight. This invention is directed toward decreasing appetite as a result of ingestion of materials that increase CCK levels.

Chemically, chitosan is a polymerized D,L-glucosamine, a polycationic molecule that is insoluble in water and in most organic solvents. However, salts of chitosan are soluble in water. Solubility of chitosan salts are determined by a number of factors, including, but not limited to, the molecular weight of the polymer, the degree of deacetylation, the counterion used, and the degree of neutralization of the polymer by the counterion. Different preparations of chitosan will vary in their ability to bind bile acids, and the most efficacious preparations for appetite control, e.g., reducing appetite and inducing satiety, will be those with the greatest ability to bind bile acids. Representative sources of chitosan include Betassane® (DVC, Inc., Wilmington, Del.), LipoSan Ultra™ (Vanson, Inc., Redmond, Wash.), Promina K® (Biopura, Rio de Mouro, Portugal), and HFP-Chitosan (Jakwang Co., Ltd., Ansung City, Korea).

Chitosan is presently used in dietary supplements to prevent absorption and metabolism of some of the ingested fat in a person's diet. Chitosan passes through the gut virtually undigested and unabsorbed. It is metabolized only to a limited extent by intestinal flora. Chitosan, due to its characteristic positively charged ions, reacts to form chitosan-lipid complexes that are able to pass through the gut without the ingested fat being absorbed or digested in the intestine. This property of chitosan makes it useful in treatments for patients with high blood lipids, hyperlipidemia, and hypercholesterolemia and weight problems. The discovery of the present invention that chitosan can be used to increase CCK levels and thereby reduce appetite and induce satiety is a distinct finding from the previously recognized ability of chitosan to promote weight control through binding and preventing the digestion of dietary fats.

Glycomacropeptide (GMP) or caseinmacropeptide is unique class of peptides derived from κ-casein. GMP is produced by hydrolysis of casein by chymosin during the cheese-making process. Glycomacropeptide is a mixture of negatively charged peptide molecules that contain about 64 amino acids, and have a molecular weight of about 6700 daltons. Glycomacropeptide molecules may exist as trimers with molecular weight of about 20,100 daltons.

Glycomacropeptide is resistant to denaturation by heat and changes in pH. GMP is unavailable commercially in pure form. However, GMP is available as a component of specially filtered whey protein isolates. These specially filtered whey protein isolates contain from about 15 to about 20% glycomacropeptide. One example is PROVON Whey Protein Isolate, sold by Glanbia Ingredients, Monroe, Wis., which typically contains about 18% GMP. Another example is Vitalarmor GMP 20, sold by Armor Proteines (Saint Brice en Cogles, France), which typically contains about 18% GMP. A third example is Carbolec Isolac sold by Carbery Group (Balineen, Ireland).

According to the present invention, compositions with wherein chitosan and GMP, which are other than in a cationic gum or polysaccharide/protein complex, are used to produce food, beverage, and dietary supplement products for appetite control, including inducing satiety and reducing appetite. Also according to the present invention, a method of controlling appetite, including inducing satiety and reducing appetite, is provided wherein compositions effective amounts of chitosan and GMP are orally administered to a human or other animal. These compositions are also intended for reducing total serum cholesterol, LDL cholesterol and blood lipids in humans and other animals in need thereof.

GMP is remarkably resistant to stomach acid and enzymes, and it can be advantageously combined with chitosan in these comestible forms. In particular, if a product of this invention is consumed just before, e.g., about fifteen minutes prior to, or during a meal, there will be rapid binding of fat, bile acids and increased release of CCK. Such increased release of CCK intensifies the onset of satiety resulting in decreased food intake. While not wishing to be bound by theory, the compositions of this invention provide a weight control benefit via two different mechanisms: (a) binding of dietary fat by dissolved chitosan to prevent fat absorption and (b) enhanced CCK production induced by both GMP and chitosan resulting in an earlier and more intense onset of satiety during consumption of a meal.

The amount of chitosan, per seving, of the present invention includes about 100 mg to about 10 g, about 200 mg to about 5 g, and about 300 mg to about 1.5 g. These masses represent the amount of chitosan per se, and do not include the mass of the counterion used to render chitosan soluble. These masses also do not include any water present in the chitosan composition. Chitosan is typically provided as a fully or partially neutralized salt of a counterion. The solubility of various chitosan preparations varies as a result of the counterions used and the degree of neutralization of the polymer.

The amount of GMP, per serving, of the present invention, includes about 5 mg to 10 g, about 10 mg to 5 g, about 25 mg to 2 g, about 100 mg–about 1000 mg, about 550 mg–about 1000 mg, and about 500 mg–about 550 mg. Glycomacropeptide is readily soluble. However, GMP, like most polypeptides, is susceptible to denaturation or degradation under conditions of elevated temperature. Therefore, conditions such as high temperature baking or batch process sterilization should be avoided or minimized in order to maintain GMP in a functional form.

The compositions of this disclosure include food, beverages, and dietary supplements. Such compositions include, but are not limited to, powder mixes, ready made beverages, yogurt, ice cream, diary milk, cheese, nutrition bars, cookies, crackers, chips, sweetbreads, confectioneries, including caramels, nougats, chocolate, hard candies, chewing gum, jelly beans, candy bars, and the like. Additionally, compositions of this invention include a wide variety of dosage forms such as capsules, tablets, chewable tablets, gel caps, and the like.

Dough for a nutrition bar can also be extruded and cut into pieces that can be baked or not baked. The pieces may also be enrobed with a confectionery coating.

Where a formulation requires pasteurization, e.g., dairy-based beverage, the formulation may be pasteurized by any method known to or within the skill of those in the art. For example, the formulation may be pasteurized at 190° F. for 5 minutes, or by ultra high temperature pasteurization in a MicroThermic unit at 285° F. for 3 seconds.

The compositions and methods of this invention can be administered to both humans and other animals. Other animals include, but are not limited to, mammals, including a member of the equine, porcine, bovine, murine, canine or feline species.

While the above compositions and methods have been described to contain both chitosan and GMP, it is also contemplated by the present invention that the compositions can contain either chitosan or GMP.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

Chocolate flavored beverage powder mix

| Ingredients | Percent | Weight (g) |
|---|---|---|
| Corn Syrup Solids, Star-Dri 200 (Staley) | 50.0000 | 850.00 |
| Carbolec Isolac Whey Protein Isolate (Carbery Foods) | 12.5000 | 212.50 |
| Food Starch, Mirathik 470 (Staley) | 10.3235 | 175.50 |
| Food Starch, Instant Textaid A (National Starch) | 10.0294 | 170.50 |
| Dutch Cocoa BV 10/12 Red Alkalized (Newton Foods) | 8.23530 | 140.00 |
| Betassane ® Chitosan Complex (DCV, Inc.) | 6.0000 | 102.00 |
| Texture Lite 5710557 (Quest International) | 0.7059 | 12.00 |
| Titanium Dioxide (Warner Jenkins) | 0.6765 | 11.50 |
| Natural & Artificial Chocolate Flavor 37288 (BBA) | 0.5882 | 10.00 |
| Natural & Artificial Cream Flavor 215642 (Givaudan Roure) | 0.2471 | 4.20 |
| Natural & Artificial Milk Flavor 480293 (Givaudan Roure) | 0.2471 | 4.20 |
| Natural & Artificial Vanilla Flavor (Givaudan Roure) | 0.1882 | 3.20 |
| Dipotassium Phosphate | 0.0941 | 1.60 |
| Sodium Silicate SIP 22SL (Degussa) | 0.0941 | 1.60 |
| Sucralose (McNeil Specialty) | 0.0588 | 1.00 |
| Black Lake #09194 (Warner Jenkins) | 0.0118 | 0.20 |
| Total | 100.0000 | 1700.00 |

The dry ingredients were weighed and blended together in a mixing bowl at low speed using a Hobart mixer for about 20 minutes. The batch was then divided into two sub-batches. Each sub-batch was blended thoroughly in a Turbula Powder Mixer (Shaker Mixer Type T2F, Bachofen AG) for about 5 minutes. The two sub-batches were then mixed together and sieved through a 600 micron screen. Any large pieces remaining on the sieve were crushed mechanically and added to the sieved material. The batch was divided again into two sub-batches, which were blended in the Turbula Powder Mixer for 5 minutes. After blending the two sub-batches together, the finished powdered beverage product was weighed in 22 gram serving portions into foil laminated pouches and heat sealed.

Example 2

Chocolate Beverage

The contents of a pouch from Example 1 can be mixed in a (what volume) 250 ml glass of water in a blender. The beverage can administered about 15 minutes prior to a meal.

Example 3

Ready-Made Soy Protein Beverage

| Ingredients | Percent | Weight (g) |
|---|---|---|
| Maltodextrin 15 DE (Staley) | 5.000 | 100.00 |
| Fine Granulated Sugar | 3.600 | 72.00 |
| Supro XT30 Soy Protein Isolate (PTI) | 3.300 | 66.00 |
| PowerPro ® Whey Protein Isolate (Land O'Lakes) | 2.200 | 44.00 |
| Sunflower Oil | 0.500 | 10.00 |
| Chitosan, LipoSan Ultra ® (Vanson Inc.) | 0.625 | 12.50 |
| Citric Acid | 0.350 | 7.00 |
| Carrageenan SD389 (FMC) | 0.300 | 6.00 |
| Avicel RC591 (FMC) | 0.150 | 3.00 |
| Sodium Hexametaphosphate, Dibasic | 0.160 | 3.20 |

-continued

Ready-Made Soy Protein Beverage

| Ingredients | Percent | Weight (g) |
|---|---|---|
| Cream Flavor #13562096 (IFF) | 0.100 | 2.00 |
| Magnesium Phosphate | 0.060 | 1.20 |
| Sodium Chloride | 0.050 | 1.00 |
| TM Cream Flavor #287496 (Givaudan Roure) | 0.050 | 1.00 |
| TM Milk Flavor #305718 (Givaudan Roure) | 0.050 | 1.00 |
| Calcium Carbonate | 0.020 | 0.40 |
| Sodium Ascorbate | 0.018 | 0.36 |
| Diacetyltartaric Acid Esters of Monoglycerides, DATEM (Danisco) | 0.015 | 0.30 |
| Vitamin Premix TM 3022 (PTI) | 0.010 | 0.20 |
| DL-Alpha-Tocopheryl Acetate (Roche) | 0.003 | 0.06 |
| Water | 83.439 | 1668.78 |
| Total | 100.000 | 2000.00 |

Using the above ingredients in the specified amounts, this beverage is prepared by dissolving citric acid in the water. The chitosan material is blended at the highest speed in a Waring blender into the dissolved citric acid in the water for about three minutes. All remaining dry ingredients are mixed together and blended in the chitosan-water solution at high speed for about 5 minutes. The mixture is then heated to 145° F. under agitation in a water-bath. All the remaining ingredients are added and blended in the hot preparation. The preparation is pasteurized by ultra high temperature pasteurization in a MicroThermic unit at 285° F. for 3 seconds. The pasteurized beverage preparation is then cooled to about 140° F. and homogenized at 5000 psi first stage and 1000 psi second stage. The finished beverage product is packaged aseptically, cooled and stored under refrigeration. This beverage has a 240 gram serving size.

Example 4
Soy Protein Beverage

The above composition is prepared just prior to consumption by omitting the pasteurization step. This beverage has a 240 gram serving size.

Reduced Calorie Nutrition Bar

| Ingredients | Percent | Weight (g) |
|---|---|---|
| Corn Syrup, 42 DE (Staley) | 30.50 | 305.00 |
| Brown Sugar | 12.50 | 125.00 |
| Instant Quick Oats (Natural Oats) | 10.63 | 106.30 |
| Crisp Rice 102 (Weetabix) | 9.40 | 94.00 |
| Raisins (Sun-Maid Growers) | 7.00 | 70.00 |
| Carbelac Isolac Whey Protein Concentrate (Carbery Foods) | 6.80 | 68.00 |
| Betassane ® Chitosan (DCV, Inc.) | 6.60 | 66.00 |
| Soybean Oil | 4.00 | 40.00 |
| All Purpose Flour | 3.00 | 30.00 |
| Fine Granulated Sugar | 2.50 | 25.00 |
| Salt | 0.40 | 4.00 |
| Cinnamon, Bakers (Dirigo Spice) | 0.40 | 4.00 |
| Lecithin (Central Soya) | 0.20 | 2.00 |
| Sodium Bicarbonate | 0.07 | 0.70 |
| Chocolate Coating | 6.00 | 60.00 |
| Total | 100.00 | 1000.00 |

Using the above ingredients in the specified amounts, the nutrition bar was prepared using a Hobart Mixer with a dough mixing spindle. Brown sugar was dissolved in the corn syrup. Chitosan was added and blended in the corn syrup at medium speed for 5 minutes. The flour, whey protein isolate, salt, cinnamon and sodium bicarbonate were added and mixed at medium speed for about 30 seconds. After admixing the raisins, oats and crisp rice, the soybean-lecithin mixture was added and mixed uniformly in the dough. The finished dough was transferred into a baking pan, covered with a wax paper and pressed with a dough roller pin to a desired thickness. The dough was baked in a pre-heated oven at 400° F. for about 15 minutes or until the dough was fully baked. The baked product was cooled to room temperature and cut into approximately 35 gram pieces. Each piece was dipped or coated with about 5 grams of chocolate coating. After cooling to allow the chocolate coating to set properly, the bars were foil-wrapped and packaged. The resulting bars contained approximately 1500 mg chitosan and 500 mg GMP per 40 gram serving size. For maximum therapeutic effect, the bar should be consumed about 15 minutes before a meal.

Example 6

Soft Chewy Confectionery

| Ingredients | Percent | Weight (g) |
|---|---|---|
| Part A | | |
| Fine Granulated Sugar | 26.00 | 260.00 |
| Corn Syrup, 42 DE (Staley) | 25.00 | 250.00 |
| Heavy Cream, 35% Fat | 8.90 | 89.00 |
| Carbelac Isolac Whey Protein Isolate (Carbery) | 6.40 | 64.00 |
| Evaporated Milk | 8.00 | 80.00 |
| Medium Invert Sugar (Domino Sugar) | 5.00 | 50.00 |
| Partially Hydrogenated Soybean Oil (Loders Croklaan) | 3.00 | 30.00 |
| Betassane Chitosan (DCV) | 2.20 | 22.00 |
| Part B | | |
| Evaporated Milk | 15.00 | 150.00 |
| Salt | 0.50 | 5.00 |
| Total | 100.00 | 1000.00 |

Using the above ingredients in the specified amounts, the soft and chewy confectionery was prepared using a Kitchen Aide mixer with a paddle. Sugar and chitosan material were mixed together and blended in the corn syrup at high speed for 5 minutes. The remaining ingredients of Part A were added and mixed with the chitosan corn syrup preparation. The preparation was transferred into a suitable container and heated to 200° F. in a water-bath under agitation. After holding the temperature at 200° F. for about 10 minutes, Part B ingredients were added and blended with Part A preparation. After raising the temperature of the mixture to 244° F., the hot sample was poured into a shallow pan and cooled in a refrigerator. After the setting process, the sample was cut into 10 gram pieces, foil-wrapped and packaged. This chewy candy product contained approximately 500 mg chitosan and 500 mg GMP per 40 gram serving size of 4 candy pieces each weighing approximately 10 grams.

Example 7

Chewable Tablet

| Ingredients | Percent | Unit Wt. Mg/Tablet | Function |
|---|---|---|---|
| Whey Protein Isolate, 20% Glycomacropeptide | 39.89 | 500 | Active |
| Chitosan, LipoSan Ultra | 23.94 | 300 | Active |
| Microcrystalline Cellulose NF, PH 102 (FMC) | 19.95 | 250 | Binder |
| Mannitol FL2080 | 15.96 | 200 | Sweetener & flavor enhancer |
| Stearic Acid | 0.16 | 2 | Lubricant |
| Orange Flavor 57.842/AP 05.51 (Firmenich) | 0.08 | 1 | Flavor |
| Sucralose | 0.02 | 0.2 | Sweetener |
| Acesulfame-K | 0.01 | 0.1 | Sweetener |
| Total | 100.0 | 1253.3 | |

Using the above ingredients in the specified amounts, the ingredients were blended together and passed through a granulator to produce a fine powdered material. After thorough mixing, the powdered material was passed through a tableting machine and compressed into chewable tablets each weighing approximately 1250 mg. Each tablet contained about 300 mg chitosan and 100 mg glycomacropeptide. A preferred serving size is 3 to 4 chewable tablets consumed about 15 minutes before a meal.

Example 8

Reduced Calorie Nutrition Bar

| Ingredients | Percent | Weight (g) |
|---|---|---|
| Corn Syrup, 42 DE (Staley) | 34.30 | 686.0 |
| Brown Sugar | 12.60 | 252.0 |
| Instant Quick Oats (Natural Oats) | 12.53 | 250.6 |
| Crisp Rice 102 (Weetabix) | 9.90 | 198.0 |
| Raisins (Sun-Maid Growers) | 7.50 | 150.0 |
| Betassane ® Chitosan (DCV, Inc.) | 6.60 | 132.0 |
| Soybean Oil | 4.00 | 80.00 |
| All Purpose Flour | 3.00 | 60.00 |
| Fine Granulated Sugar | 2.50 | 50.00 |
| Salt | 0.40 | 8.00 |
| Cinnamon, Bakers (Dirigo Spice) | 0.40 | 8.00 |
| Lecithin (Central Soya) | 0.20 | 4.00 |
| Sodium Bicarbonate | 0.07 | 1.40 |
| Chocolate Coating | 6.00 | 120.0 |
| Total | 100.00 | 2000.0 |

Using the above ingredients in the specified amounts, corn syrup and the sugars were combined in a glass beaker. Chitosan was added and hydrated in the sugar syrup by stirring at 1200 rpm with a Lightning mixer for about 5 minutes. The preparation was transferred into a lab Hobart mixer with a dough spindle. Flour, salt, cinnamon and bicarbonate were added and mixed together at low speed for about 60 seconds. The raisins, oats and crisp rice were admixed with the dough for about 60 seconds. A blend of the soybean oil and lecithin was mixed uniformly in the dough. The finished dough was transferred into a baking pan and covered with wax paper. After pressing the dough with a dough roller pin to a desired thickness, the sample was baked in a pre-heated oven at 400° F. for about 15 minutes and cooled to room temperature. The fully baked sample was cut into pieces approximately of 40-gram or 35-gram pieces. The 40-gram pieces were foil-wrapped and packaged. The 35-gram pieces were dipped or coated with about 5 grams of chocolate or a confectionery coating. After cooling to allow the coating to set, the samples are foil-wrapped and packaged. The resulting product contained approximately 1500 mg chitosan in a 40-gram serving size. For optimum results this composition should be consumed approximately 15 minutes before a meal.

Example 9

Clinical Trial And Design

The purpose of this clinical trial is to confirm the effects of chitosan, optionally with GMP, in reducing appetite and inducing satiety. This study involves a crossover design in which each subject randomly consumes on different occasions a product containing chitosan, optionally with GMP, or a placebo of similar texture and taste.

Preferably the study involves 20 subjects, male or female, between 21 and 70 years of age. Subjects should not have major underlying metabolic problems (e.g. diabetes or hypertension), and should be consuming a normal diet. On each test date, the subjects arrive at the clinic in a fasted state. The subjects then consume a product containing chitosan and, optionally, GMP as disclosed herein, for example such as that disclosed in Example 1, or an isocaloric placebo product of similar taste and texture. Fifteen minutes after consuming the product, the subjects then consume a standard meal such as Stouffer's® Macaroni and Beef with Tomatoes, a frozen single dish meal containing 380 calories that is heated in a microwave before serving. Subjects are permitted to consume water with this meal. For three and one-half hours after consuming the meal, every 15 minutes the subjects complete a form to determine their sensations of hunger and satiety. The form contains a series of visual analog scales of 100 mm width. At either end of the scale, descriptive words are printed indicating the extreme levels of fullness or hunger that a subject might be feeling. The subject draws a line vertically through a point on the line indicating his or her physical response to either fullness or hunger. Data are statistically analyzed to determine the diminution of hunger and the increase in satiety resulting from consumption of product containing the appetite control agent versus the placebo. Optionally, after three and three quarters hours, subjects will be offered an open-ended meal of Kraft® macaroni and cheese dinner. Portions of the macaroni and cheese will be weighed before and after eating so that total calories consumed by each subject can be calculated. These data are also analyzed to determine the effects of the product with chitosan and, optionally, GMP on decreasing food consumption during this second meal.

At intervals of 30, 60, and 120 minutes following ingestion of the test or placebo product, blood samples are drawn into 10 ml tubes containing EDTA and aprotenin, a protease inhibitor that blocks degradation of CCK in the samples. The blood samples are chilled immediately on ice, and plasma is separated in a refrigerated centrifuge. The plasma is immediately frozen at −20° C. or colder. CCK levels are determined by radioimmunoassay, such as for example with the Euria-CCK kit sold by Euro Diagnostica, Malmo, Sweden. Results of the CCK analyses are analyzed to determine the increase in blood CCK levels resulting from consumption of chitosan and, optionally, GMP.

What is claimed is:

1. A composition for oral administration comprising chitosan and GMP, wherein the chitosan and GMP are in other than a cationic gum or polysaccharide/protein complex.

2. A composition according to claim 1 containing from about 100 mg to about 10 g of chitosan and from about 5 mg to about 10 g of GMP.

3. A composition of claim 1 containing from about 100 mg to about 10 g of chitosan.

4. A composition of claim 3 containing from about 200 mg to about 5 g of chitosan.

5. A composition of claim 4 containing from about 500 mg to about 1.5 g of chitosan.

6. A composition of claim 1 containing from about 5 mg to about 10 g of GMP.

7. A composition of claim 6 containing from about 10 mg to about 5 g of GMP.

8. A composition of claim 7 containing from about 25 mg to about 2 g of GMP.

9. A composition of claim 2 containing from about 500 mg to about 1.5 g of chitosan and from about 25 mg to about 2 g of GMP.

10. A composition of claim 1 wherein the composition for ingestion is selected from the group consisting of a food, a beverage, and a dietary supplement.

11. A composition of claim 10 wherein the food is selected from the group consisting of a bar, cookie, cracker, cereal, and confectionery form.

12. A composition of claim 10 wherein the beverage is a prepared beverage.

13. A composition of claim 10 wherein the beverage is a dry mix.

14. A composition of claim 10 wherein the dietary supplement is selected from the group consisting of a tablet, a caplet, a capsule, a softgel and a powder.

15. A method for controlling appetite in a human comprising orally administering a composition containing chitosan and GMP, wherein the chitosan and GMP are in other than a cationic gum or polysaccharide/protein complex.

16. A method of claim 15 wherein the composition comprises from about 100 mg to about 10 g of chitosan and from about 5 mg to about 10 g of GMP.

17. A method of claim 15 comprising orally administering a composition containing from about 100 mg of chitosan to about 10 g of chitosan.

18. A method of claim 17 comprising orally administering a composition containing from about 200 mg of chitosan to about 5 g of chitosan.

19. A method of claim 18 comprising orally administering a composition containing from about 500 mg to about 1.5 g of chitosan.

20. A method of claim 15 comprising orally administering a composition containing from about 5 mg to about 10 g of GMP.

21. A method of claim 20 comprising orally administering a composition containing from about 10 mg to about 5 g of GMP.

22. A method of claim 21 comprising orally administering a composition containing from about 25 mg to about 2 g of GMP.

23. A method of claim 16 comprising orally administering a composition containing from about 500 mg to about 1.5 g of chitosan and from about 25 mg to about 2 g of GMP.

24. A method of claim 15 wherein the composition is selected from the group comprising a food, a beverage, and a dietary supplement.

25. A method of claim 24 wherein the food is selected from the group consisting of a bar, cookie, cracker, cereal, and a confectionery.

26. A method of claim 24 wherein the beverage is a prepared beverage.

27. A method of claim 24 wherein the beverage is prepared from a dry mix.

28. A method of claim 24 wherein the composition is a dietary supplement selected from the group consisting of a tablet, a caplet, a capsule, a softgel, and a powder.

29. A method for controlling appetite in an animal comprising orally administering a composition comprising chitosan and GMP, wherein the chitosan and GMP are in other than a cationic gum or polysaccharide/protein complex.

30. A method as claimed in claim 29 wherein the animal is obese.

31. A method of claim 28 wherein the composition comprises from about 100 mg to about 10 g of chitosan.

32. A method of claim 28 wherein the composition comprises from about 200 mg to about 5 g of chitosan.

33. A method of claim 32 wherein the composition contains from about 500 mg to about 1.5 g of chitosan.

34. A method of claim 29 wherein the composition is selected from the group consisting of a food, a beverage, and a dietary supplement.

35. A method of claim 34 wherein the food is selected from the group consisting of a bar, cookie, cracker, cereal, and confectionery form.

36. A method of claim 34 wherein the beverage is selected from a group consisting of a prepared beverage and a beverage prepared from a dry mix.

37. A method of claim 34 wherein the dietary supplement is selected from the group consisting of a tablet, a caplet, a capsule, a softgel, and a powder.

* * * * *